United States Patent [19]

McGurk-Burleson et al.

[11] Patent Number: 4,850,354
[45] Date of Patent: Jul. 25, 1989

[54] SURGICAL CUTTING INSTRUMENT

[75] Inventors: Erin McGurk-Burleson, Clemente, Calif.; Elmer Koehler, St. Louis, Mo.; Victor S. Packham, Santa Ana, Calif.

[73] Assignee: Baxter Travenol Laboratories, Inc., Deerfield, Ill.

[21] Appl. No.: 85,643

[22] Filed: Aug. 13, 1987

[51] Int. Cl.⁴ .............................................. A61B 17/32
[52] U.S. Cl. ..................................... 128/305; 604/22; 30/29.5; 30/240
[58] Field of Search ............... 128/305, 312, 313, 318, 128/751, 755; 604/22; 30/264, 240, 29.5, 347

[56] References Cited

U.S. PATENT DOCUMENTS

| | | | |
|---|---|---|---|
| D. 219,252 | 11/1970 | Bogoff | D24/3 |
| 2,729,210 | 1/1956 | Spencer | 128/2 |
| 3,618,611 | 11/1971 | Urban | 128/305 |
| 3,815,604 | 6/1974 | O'Malley et al. | 128/305 |
| 3,945,375 | 3/1976 | Banko | 128/6 |
| 3,990,453 | 11/1976 | Douvas et al. | 128/305 |
| 4,099,529 | 7/1978 | Peyman | 128/305 |
| 4,111,207 | 9/1978 | Seiler, Jr. | 123/305 |
| 4,203,444 | 5/1980 | Bonnell et al. | 128/276 |
| 4,274,414 | 6/1981 | Johnson et al. | 128/305 |
| 4,598,710 | 7/1986 | Kleinberg et al. | 128/318 |
| 4,603,694 | 8/1986 | Wheeler | 128/312 |

OTHER PUBLICATIONS

Storz New Precision Arthroplasty System . . . , Storz Instrument Company, Orthopedic Division, St. Louis, Mo. 1984 (4 pages).
New and Controversial Aspects of Vitreoretinal Surgery, "The Visc and the Vitreomicroscope", Jean-Marie Parel, C.V. Mosby Co., St. Louis (1977).

Primary Examiner—Andrew M. Dolinar
Attorney, Agent, or Firm—Gordon L. Peterson

[57] ABSTRACT

A surgical cutting instrument comprising an outer tube having a peripheral wall, an end wall and an opening in the peripheral wall and the end wall. The outer tube has first and second cutting edges defining portions of the periphery of the opening, and the cutting edges intersect at an angle of at least about 90 degrees to define a corner. An inner cutting member is rotatable within the outer tube. The inner cutting member has a cutting edge cooperable with both the first and second cutting edges of the outer tube for cutting material with a shearing action that progresses along both of the first and second cutting edges toward the corner.

11 Claims, 2 Drawing Sheets

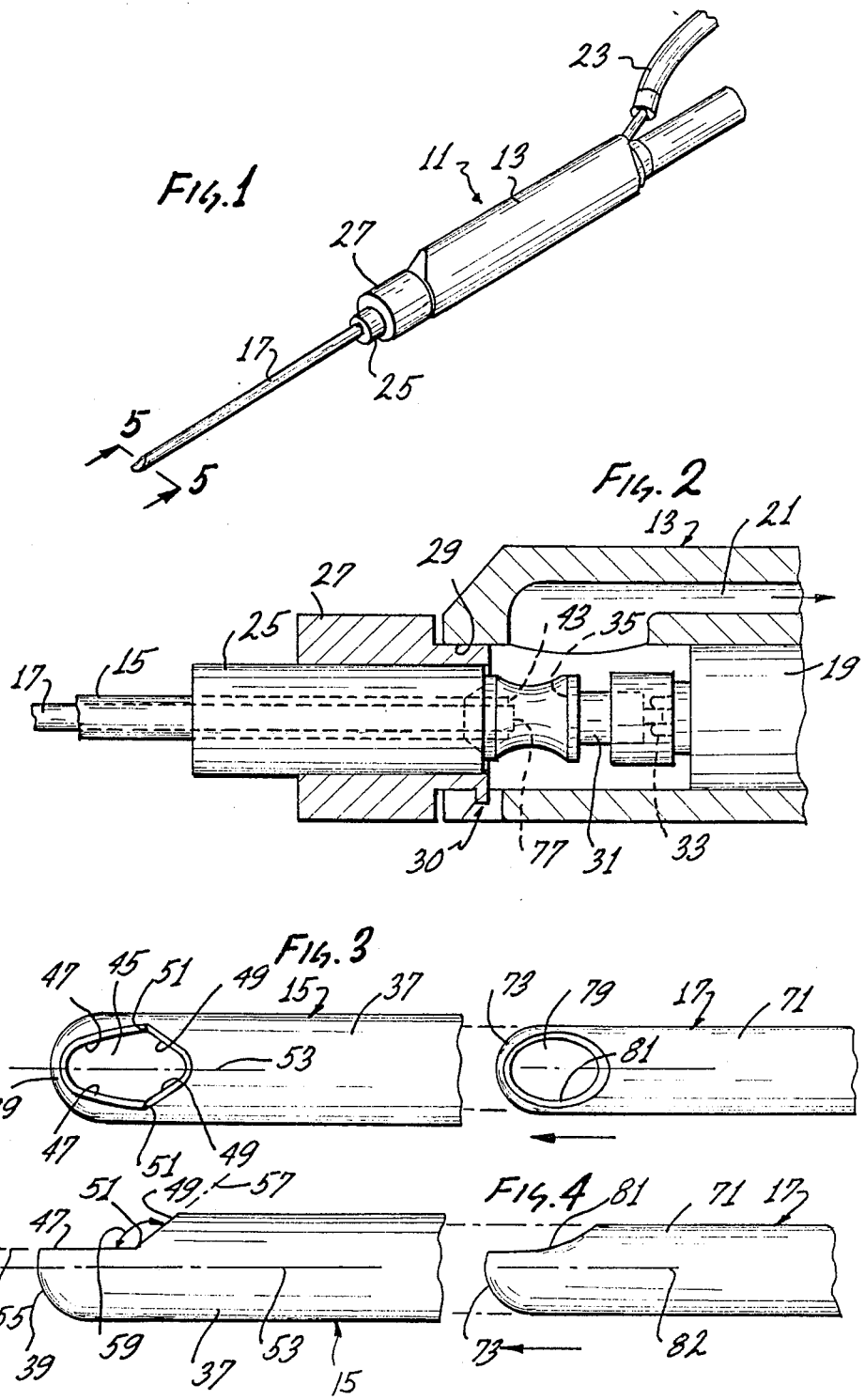

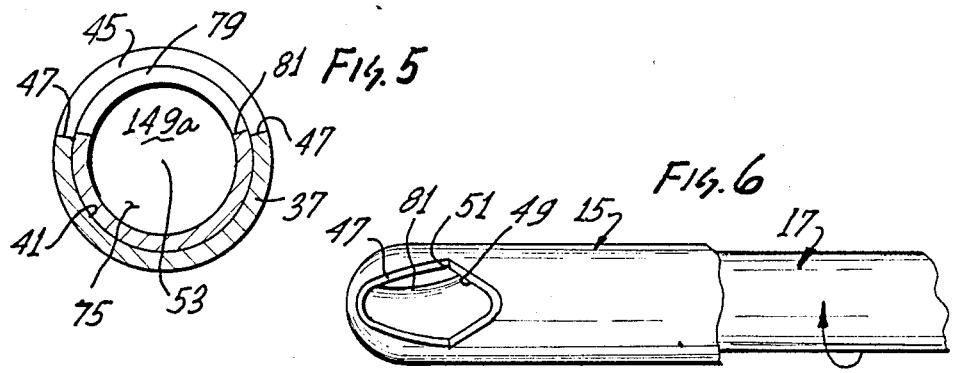
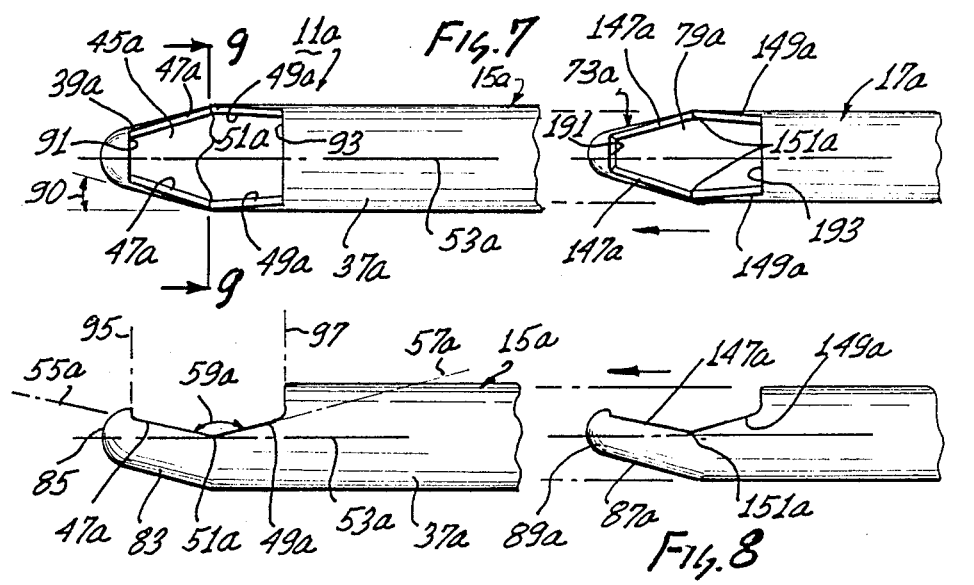
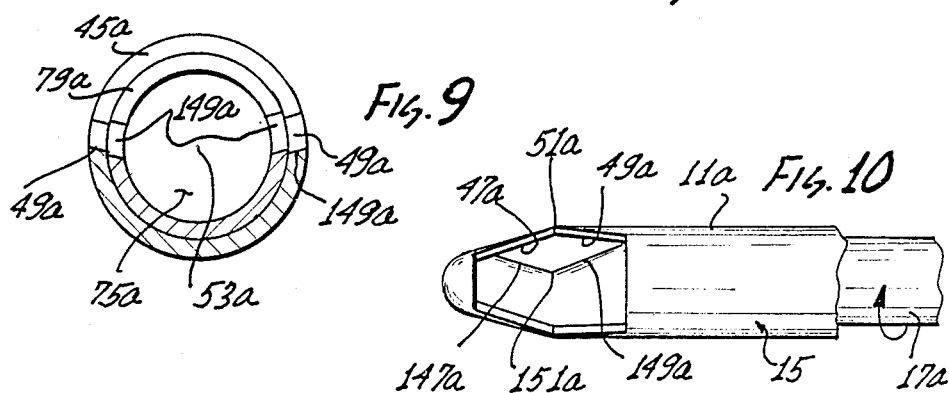

SURGICAL CUTTING INSTRUMENT

BACKGROUND OF THE INVENTION

This invention relates to a surgical cutting instrument of the type employing rotary cutters. Instruments of this type are usable for various surgical procedures in various regions of the body, such as in the eye and knee. For example, the surgical cutting instrument may be inserted through a small opening into the knee joint and used for cutting the meniscus or other soft or hard tissue or material.

Generally, a surgical cutting instrument of this type includes an outer tube having a peripheral wall, an end wall, an opening in one or both of the peripheral wall and the end wall and a cutting edge defining at least a portion of the periphery of the opening. An inner cutting member, which may also be in the form of a tube, rotates or translates within the outer tube. The inner cutting member has a cutting edge that cooperates with the cutting edge of the outer tube for cutting material with a shearing action as the inner cutting member is moved relative to the outer tube. One surgical cutting instrument of this general type is shown and described in Johnson et al U.S. Pat. No. 4,274,414.

Notwithstanding the proliferation of known configurations for the outer tube and the inner cutting member, there are problems with poor cutting ability and inconsistent quality. The poor cutting ability increases the likelihood of clogging, and many constructions are unable to reach relatively inaccessible areas, such as areas within the knee joint where space is at a premium.

SUMMARY OF THE INVENTION

This invention provides a novel surgical cutting instrument having various different features which tend to solve the problems identified above. According to one feature of this invention, shearing action progresses along two separate cutting edges toward a corner, and the material being cut is trapped in the corner and prevented from escaping. Consequently, the cutting ability is improved, consistency is enhanced and the likelihood of clogging is reduced. This is accomplished with a relatively large area opening of the outer tube.

The invention can advantageously be embodied in a surgical cutting instrument which includes an outer tube sized for insertion through an opening in a patient with the outer tube having a peripheral wall, an end wall, and an opening in the peripheral wall and the end wall. The outer tube has first and second cutting edges which define portions of the periphery of the opening, and the first and second cutting edges substantially intersect at an angle of at least about 90 degrees to define a corner. An inner cutting member is rotatable within the outer tube. The inner cutting member has a cutting edge cooperable with both the first and second cutting edges of the outer tube for cutting material from within a patient with a shearing action.

With this construction, the shearing action progresses along two cutting edges, and as it does, it crowds the material to be cut toward the corner so that it is more difficult for it to escape. The shearing action is enhanced by having the first and second cutting edges substantially intersect at an included angle of 90 degrees or greater. Preferably, the angle is obtuse and in the range of 90 degrees to 170 degrees with about 130 degrees being preferred for some constructions. Angles less than 90 degrees tend to unduly reduce the size of the opening, and angles over 170 degrees tend to reduce the effect of the corner.

The ability of the surgical cutting instrument to trap material at the corner is enhanced if the corner is sharp, i.e., not radiused or formed by only a very small radius. Accordingly, it is preferred to have an essentially small radiused corner toward which the shearing action progresses. It is not, however, necessary that the shearing action terminate simultaneously along both cutting edges at the corner.

By having the opening in the outer tube open in both the peripheral wall and the end wall, cutting can proceed both laterally and axially of the outer tube. This also enlarges the opening of the tube.

The inner cutting member can be tubular or non-tubular so long as it provides a cutting edge that cooperates with both of the cutting edges of the outer tube as described above. Preferably, however, the inner cutting member includes an inner tube having an opening therein, with the cutting edge of the inner tube extending along the periphery of the opening. Although the opening can be of various different configurations, one preferred configuration is oval because an oval opening can be used with a multiplicity of different opening configurations of the outer tube. Also, the opening of the inner tube can match the opening of the outer tube, if desired.

The outer tube has a longitudinal axis, and the opening is preferably formed at least in part by a plane which extends distally as it extends radially inwardly to form an acute angle with the longitudinal axis. According to one preferred embodiment, the opening of the outer tube may be visualized as formed at least in part by reference planes which intersect on one side of the axis, with the first plane being generally parallel to the axis, and the second plane entering the outer tube from said one side and forming an obtuse angle with the second plane such that the intersection of the planes forms the corner.

According to another feature of this invention, the end wall of the outer tube is constructed to enter small, relatively inaccessible spaces to enable the instrument to perform a cutting operation at these locations. For this purpose, the end wall may include a generally rounded distal tip section and a tapered section which is of progressively reducing cross section as it extends distally. The tapered section, which is preferably conical, joins the tip section, which is preferably generally part-spherical, to the peripheral wall. An important feature is that the opening in the outer tube is in both the peripheral wall and the end wall, with the opening preferably extending for substantially the full axial length of the tapered section. This provides a relatively large opening and enables cutting action to occur both axially and radially. In a preferred construction, the angle of taper of the tapered section is from about 10 degrees to about 20 degrees, and the axial dimension of the end wall is greater than the diameter of the peripheral wall. In a preferred construction, the opening of the outer tube may be visualized at least in part by planes which intersect to form the corner, with the planes extending in the same direction radially and in opposite directions axially as they extend away from the corner.

The invention, together with additional features and advantages thereof, may best be understood by reference to the following description taken in connection with the accompanying illustrative drawings.

BRIEF DESCRIPTION OF THE DRAWINGS

FIG. 1 is an isometric view of a surgical cutting instrument constructed in accordance with the teachings of this invention.

FIG. 2 is an enlarged fragmentary sectional view illustrating the coupling of the outer tube and the inner cutting member to the handle.

FIG. 3 is a fragmentary, exploded top plan view of the distal regions of the inner and outer tubes.

FIG. 4 is a side elevational view of the construction shown in FIG. 3.

FIG. 5 is an enlarged sectional view taken generally along line 5—5 of FIG. 1.

FIG. 6 is a top plan view of the distal region of the surgical cutting instrument showing how the cutting edges cooperate to cut material.

FIGS. 7 and 8 are top plan and side elevational views, respectively, similar to FIGS. 3 and 4, respectively, illustrating a second embodiment of the invention.

FIG. 9 is an enlarged sectional view taken generally along line 9—9 of FIG. 7, with the inner tube being fully inserted into the outer tube.

FIG. 10 is a top plan view of the distal region of the surgical cutting instrument showing how the cutting edges cooperate to cut material.

DESCRIPTION OF THE PREFERRED EMBODIMENTS

FIGS. 1-6 show a surgical cutting instrument 11 which generally comprises a handle 13, an outer tube 15, and an inner cutting member in the form of an inner tube 17. The inner tube 17 is slidably receivable and rotatable within the outer tube 15. The outer tube 15 is fixedly attached to the handle 13 in a known manner, and the inner tube 17 is drivable by a motor 19 carried by the handle 13. The handle 13 also provides a passage 21 which is coupled by a conduit 23 (FIG. 1) to a vacuum source (not shown) for applying suction pressure to the interior of the inner tube 17 to withdraw material severed during operation of the cutting instrument.

More specifically and by way of example, a sleeve 25 is suitably fixedly attached to the outer tube 15, and the sleeve in turn is releasably mounted on a collar 27 in a conventional manner, such as by ball detents and a key and keyway (not shown). The collar 27 is removably received within a bore 29 of the handle 13 by a conventional quick disconnect connection 30. The inner tube 17 extends proximally of the sleeve 25 where it is coupled by a conventional coupling 31 to a drive shaft 33 (FIG. 2) of the motor 19. With this construction, the motor 19 can rotate the inner tube 17 within the outer tube 15 in a known manner. Vacuum pressure may be applied to the interior of the inner tube 17 via the passage 21 and a radial opening 35 in the coupling 31 in a conventional manner. The bearing support for the rotation of the inner tube 17 can be provided in whole or in part by the outer tube 15 or in any other suitable manner known in the art.

The outer tube 15 is sized for insertion through an opening, such as a puncture or incision, in a patient. For example, the outer tube may be sized for insertion through an opening in the knee and may be used, for example, for cutting cartilage in the knee.

The outer tube 15 has a peripheral wall 37 and an end wall 39 at a distal end of the outer tube. Although various configurations are possible, the peripheral wall 37 is preferably cylindrical, and the end wall, in this embodiment, is preferably generally hemispherical and of the same radius as the peripheral wall. The outer tube 15 has a passage 41 (FIG. 5) which extends completely through the outer tube from a proximal end 43 (FIG. 2) all the way to the end wall 39 at the distal end of the outer tube. The passage 41 is cylindrical throughout the full length of the peripheral wall 37 and is hemispherical within the hemispherical end wall 39.

The outer tube 15 has an opening 45 in the peripheral wall 37 and the end wall 39. This invention differs from the prior art in the configuration and function of the opening 45 and in its cooperation with the inner tube 17.

The outer tube 15 has cutting edges 47 and 49 defining portions of the periphery of the opening 45 and intersecting at an obtuse angle to define a corner 51. In this embodiment, the opening 45 is symmetrical about a longitudinal axis 53 of the outer tube 15 (FIG. 2), and accordingly, there are two sets of cutting edges 47 and 49 and two corners 51 as illustrated. The cutting edges 49 are in the peripheral wall 37, and the cutting edges 47 lie in both the peripheral wall and the end wall 39. With this construction, the cutting edges 47 are blended together in a smooth curve as are the cutting edges 49, all as shown in FIG. 2.

Viewed from a different perspective, the opening 45 may be visualized as formed by planes 55 and 57 (FIG. 4) which intersect on one side of the axis 53. The plane 55 is generally parallel to the axis 53, and the plane 57 enters the outer tube 15 from such one side and forms an obtuse angle 59 with the plane 55. The intersection of the planes 55 and 57 forms the corners 51. The planes 55 and 57 preferably intersect such that the corner 51 is formed with essentially no radius. However, a small radius at the corner 51 is acceptable. In actual practice, the opening 45 may be formed by one or more rotating cutting tools, and so reference herein to the planes 55 and 57 is only for the purpose of describing the basic geometry of the opening and not for the purpose of describing a method of manufacture. Also, the edges 47 and 49 may be beveled, if desired, in a manner that the planes 55 and 57 could not produce.

The angle 59 should be at least 90 degrees and is preferably in the range of 90 degrees to 150 degrees with about 130 degrees being preferred. With this arrangement, the plane 57 extends distally as it extends radially inwardly and forms an acute angle (the supplement of the angle 59) with the longitudinal axis 53. Although the corners 51 could be below the axis 53 as viewed in FIG. 4, preferably they lie above the axis to avoid unduly structurally weakening the distal tip region of the outer tube 15.

Although the inner tube 17 can be of various different constructions, in this embodiment, it includes a cylindrical, peripheral wall 71 and a hemispherical end wall 73 at the distal end of the inner tube. The inner tube 17 has a passage 75 which extends from a proximal end 77 (FIG. 2) of the inner tube all the way to the end wall 73.

The inner tube 17 has an opening 79 and a cutting edge 81 extending along the periphery of the opening 79 and completely circumscribing the opening. The cutting edge 81 can be of any configuration that will appropriately cooperate with the cutting edges 47 and 49 to shear material to be cut in a scissors-like fashion while crowding such material generally toward the associated corner 51. In this embodiment, the opening 79 and the cutting edge 81 are generally oval, and more specifically, are generally elliptical as shown in FIG. 3. The opening 79 can be of various other configurations, including a configuration which matches the configuration of the opening 45 of the outer tube 15. In addition, an appropriate cutting edge may be provided on a nontubular rotatable member, such as a helix, if desired.

As shown in FIG. 4, the cutting edge 81 and, therefore, the opening 79 are in both the peripheral wall 71 and the end wall 73. The cutting edge 81 appears elliptical as viewed in FIG. 3 and forms an arc as shown in FIG. 4 which lies entirely above a central longitudinal axis 82 of the inner tube 17.

In use of the cutting instrument 11, it is inserted through an opening in the knee to a region, such as the meniscus, which is to be cut, and the motor 19 is energized to begin unidirectional rotation of the inner tube 17 within the outer tube 15. This moves the cutting edge 81 along the cutting edges 47 and 49 toward the corner 51 as generally illustrated in FIG. 6 to provide shearing or scissors-like cutting action along both of the cutting edges 47 and 49 while crowding tissue toward the corner 51. This provides reliable and effective cutting of the tissue along the two intersecting cutting edges 47 and 49 in such a way that consistency and cutting efficiency are enhanced. Suction is applied through the passage 21, the opening 35 and the passage 75 of the inner tube 17 so as to remove severed material after it is cut so that the cutting instrument need not be withdrawn from the incision to accomplish this. Because the opening 45 is symmetrical about the axis 53, the inner tube 17 can be rotated in either direction within the outer tube 15, and the same desirable cutting action is achieved.

FIGS. 7-10 show a cutting instrument 11a which is identical to the cutting instrument 11 in all respects not shown or described herein. Portions of the cutting instrument 11a corresponding to portions of the cutting instrument 11 are designated by corresponding reference numerals followed by the letter "a."

The primary difference between the cutting instruments 11 and 11a is in the configuration of the openings 45a and 79a and in the shape of the end walls 39a and 73a.

More specifically, the end wall 39a comprises a generally conical tapered section 83 and a generally partspherical section 85, with the conical section being of reduced diameter as it extends distally and integrally joining the peripheral wall 37a to the spherical section 85. The inner tube 17a is similarly constructed in that it comprises a conical section 87a and a spherical section 89a. In this embodiment, the conical section 83 has an angle of taper of about 15 degrees, and the axial dimension of the end wall 39a is a bit greater than the outside diameter of the peripheral wall 37a.

The opening 45a has cutting edges 47a and 49a which intersect to form an angle 59a (FIG. 8) of greater than 90 degrees and which, in this embodiment, is about 155 degrees. The cutting edges 47a and 49a intersect at a corner 51a. The opening 45a is symmetrical about the axis 53a, and so there are two sets of the cutting edges 47a and 49a and two of the corners. The cutting edges 47a and 49a are joined by edges 91 and 93, respectively.

Viewed from a different perspective, the opening 45a is formed in part by planes 55a and 57a which intersect to form the corners 51a and which extend in the same direction radially and in opposite directions axially as they extend away from the corners 51a as shown in FIG. 8. The corners 51a lie substantially on the axis 53a as viewed in side elevation as shown in FIG. 8. The corners 51a also lie at the juncture of the end wall 39a and the peripheral wall 37a. Thus, the cutting edges 47a lie in the conical section 83, and the cutting edges 49a lie in the peripheral wall 37a. As shown in FIG. 8, the cutting edges 47a and 49a terminate at locations remote from the corners 51a which lie radially inwardly of the periphery of the outer tube 15a. Also, as shown in FIG. 8, the edges 91 and 93 are formed by axially spaced, radial planes 95 and 97, respectively, which intersect the planes 55a and 57a at locations spaced from, and on the same side of, the axis 53a.

The opening 79a and the associated cutting edges are identical to the opening 45a and its cutting edges, and accordingly, corresponding portions of the opening 79a and the associated cutting edges are designated by corresponding reference characters preceded by the numeral "1." The only difference between the openings 79a and 45a is that the cutting edges 147a and 149a are on the outside diameter of the inner tube 17a rather than along the inside diameter as is the case with the outer tube 15a.

The operation of the cutting instrument 11a is essentially as described above for the cutting instrument 11. In this regard, the shearing or scissors action proceeds along the cutting edges 47a and 49a toward the corner 51a by virtue of the cooperation between the cutting edges 47a and 147a and the cutting edges 49a and 149a. The material being cut tends to be trapped in the corner 51a and is prevented from escaping. In addition, with this embodiment, the shearing action terminates essentially simultaneously along the cutting edges 47a and 49a at the corner 51a; whereas, with the cutting instrument 11, the shearing action along the cutting edge 49 is complete slightly before the completion of the shearing action along the cutting edge 47.

Although exemplary embodiments of the invention have been shown and described, many changes, modifications and substitutions may be made by one having ordinary skill in the art without necessarily departing from the spirit and scope of this invention.

We claim:
1. A surgical cutting instrument comprising:
an outer tube sized for insertion through an opening in a patient, said outer tube having a peripheral wall and an end wall;
said outer tube having an opening in said peripheral wall and said end wall;
said outer tube having first and second cutting edges defining portions of the periphery of the opening and substantially intersecting at an angle of at least about 90 degrees to define a corner;
an inner cutting member rotatable within said outer tube;
said inner cutting member having a cutting edge cooperable with both said first and second cutting edges of the outer tube for cutting material from within the patient with a shearing action that progresses along both said first and second cutting edges toward said corner as the inner cutting member rotates; and
the outer tube having a longitudinal axis and said opening being formed at least in part by first and second planes which intersect on one side of said axis, said first plane being generally parallel to said axis and said second plane entering the outer tube from said one side and forming an obtuse angle with the first plane, and the intersection of said planes forming said corner.

2. An instrument as defined in claim 1 wherein said inner cutting member includes an inner tube rotatable within said outer tube and having an opening therein, and said cutting edge of said inner tube extends along the periphery of the opening in the inner tube.

3. An instrument as defined in claim 2 wherein said opening in said inner tube is generally oval.

4. An instrument as defined in claim 1 including a handle, a motor carried by the handle, means for mounting the outer tube on the handle and means for coupling the inner cutting member to the motor so that the motor can rotate the inner cutting member.

5. An instrument as defined in claim 1 wherein said peripheral wall is generally cylindrical and at least a portion of said end wall is part spherical.

6. A surgical cutting instrument comprising:
an outer tube sized for insertion through an opening in a patient, said outer tube having a peripheral wall and an end wall;
said outer tube having an opening in said peripheral wall and said end wall;
said outer tube having first and second cutting edges defining portions of the periphery of the opening and substantially intersecting at an angle of at least about 90 degrees to define a corner;
an inner corner member rotatable within said outer tube;
said inner cutting member having a cutting edge cooperable with both said first and second cutting edges of the outer tube for cutting material from within the patient with a shearing action that progresses along both said first and second cutting edges toward said corner as the inner cutting member rotates; and
the outer tube having a longitudinal axis and a substantial portion of said opening is formed by first and second planes which intersect to form said corner and which extend in the same direction radially and in opposite directions axially as they extend away from said corner.

7. An instrument as defined in claim 6 wherein said end wall comprises a generally conical section and a generally part spherical section.

8. An instrument as defined in claim 7 wherein said first and second planes extend into the conical section and the part-spherical section, respectively.

9. An instrument as defined in claim 6 wherein said cutting edges terminate at locations remote from said corner which lie radially inwardly of the periphery of the outer tube.

10. An instrument as defined in claim 9 wherein said corner is substantially on said axis as viewed in side elevation with respect to said first and second plane and lies substantially in a radial plane at the juncture of the end wall and the peripheral wall.

11. An instrument as defined in claim 9 wherein said end wall comprises a generally conical section and a generally part spherical section.

* * * * *

UNITED STATES PATENT AND TRADEMARK OFFICE
CERTIFICATE OF CORRECTION

PATENT NO. : 4,850,354

DATED : July 25, 1989

INVENTOR(S) : Erin McGurk-Burleson et al

It is certified that error appears in the above-identified patent and that said Letters Patent is hereby corrected as shown below:

Column 7, line 26 change "corner member" to -- cutting member --.

Signed and Sealed this

Seventeenth Day of July, 1990

*Attest:*

HARRY F. MANBECK, JR.

*Attesting Officer*     *Commissioner of Patents and Trademarks*